United States Patent [19]

Tanaka et al.

[11] Patent Number: 4,752,650

[45] Date of Patent: Jun. 21, 1988

[54] PHOTORECEPTOR FOR ELECTROPHOTOGRAPHY

[75] Inventors: Hiroyuki Tanaka; Seki Kin; Lyong S. Pu, all of Kanagawa, Japan

[73] Assignee: Fuji Xerox Co., Ltd., Tokyo, Japan

[21] Appl. No.: 91,340

[22] Filed: Aug. 31, 1987

Related U.S. Application Data

[63] Continuation of Ser. No. 682,203, Dec. 17, 1984, abandoned.

[30] Foreign Application Priority Data

| | | | |
|---|---|---|---|
| Dec. 16, 1983 | [JP] | Japan | 58-236203 |
| Dec. 16, 1983 | [JP] | Japan | 58-236204 |
| Dec. 16, 1983 | [JP] | Japan | 58-236205 |

[51] Int. Cl.[4] .................. C07C 85/00; C07C 85/02; C07C 85/06

[52] U.S. Cl. .................. 564/307

[58] Field of Search .................. 564/307

[56] References Cited

U.S. PATENT DOCUMENTS

| | | | |
|---|---|---|---|
| 4,353,971 | 10/1982 | Chang et al. | 430/58 |
| 4,521,621 | 6/1985 | Yanus et al. | 564/307 |
| 4,523,035 | 6/1985 | Yanus | 564/307 |
| 4,524,218 | 6/1985 | Baranyi et al. | 564/307 |

FOREIGN PATENT DOCUMENTS

| | | | |
|---|---|---|---|
| 57-144558 | 9/1982 | Japan | 564/307 |

*Primary Examiner*—Paul F. Shaver

*Attorney, Agent, or Firm*—Sughrue, Mion, Zinn, Macpeak & Seas

[57] ABSTRACT

Novel squarylium compounds, a process for the production thereof as well as to a photoreceptor for electrophotography containing the squarylium compound are disclosed, said squarylium compounds being represented by formula (I) or (II):

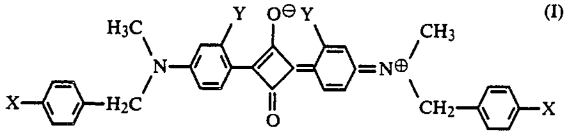

(I)

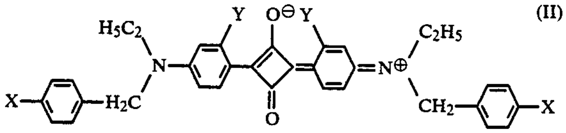

(II)

wherein X is a hydrogen atom, an alkyl group having 1 to 6 carbon atoms, a hydroxyl group, an alkoxy group having 1 to 4 carbon atoms, or a halogen atom; Y is a hydrogen atom, an alkyl group having 1 to 4 carbon atoms, a hydroxyl group or an alkoxyl group having 1 to 4 carbon atoms.

10 Claims, 1 Drawing Sheet

PHOTORECEPTOR FOR ELECTROPHOTOGRAPHY

This is a continuation of application Ser. No. 682,203, filed 12/17/84, now abandoned.

FIELD OF THE INVENTION

The present invention relates to a novel squarylium compound and a process for the production thereof, as well as to a photoreceptor for electrophotography containing the squarylium compound.

BACKGROUND OF THE INVENTION

Common photoreceptors for use in electrophotography are inorganic light-sensitive materials such as amorphous selenium, selenium compounds, cadmium sulfide and zinc oxide, as well as organic compounds typified by poly(vinylcarbazole) and poly(vinylcarbazole) derivatives.

As is well known, amorphous selenium and selenium alloys have excellent properties for use as electrophotographic photoreceptors and are commercially used. However, their manufacture requires the complex step of vapor deposition, and the vapor deposited film has no flexibility. Zinc oxide as a photoreceptor material is dispersed in a resin to prepare a disperse light-sensitive composition, but this has low mechanical strength and is not suitable for cyclic use.

Poly(vinylcarbazole) widely known as an organic photoconductive material is advantageous with respect to transparency, film-forming properties and flexibility. However, poly(vinylcarbazole) per se is insensitive to light in the visible range and cannot be immediately used as a photoreceptor. Various methods have been proposed for sensitizing the poly(vinylcarbazole). The use of a sensitizing dye is effective in extending the spectral sensitivity of the poly(vinylcarbazole) to the visible range, but the sensitivity of the so treated polyvinyl carbazole is still insufficient for use as an electrophotographic photoreceptor and it undergoes significant fatigue under light illumination. When poly(vinylcarbazole) is chemically sensitized with an electron acceptor compound, sufficient sensitivity for use as an electrophotographic photoreceptor is obtained. Several of the so treated poly(vinylcarbazole) compounds are commercially used, but their mechanical strength and service life are still unsatisfactory.

Among photoreceptors having sensitivity to light in the longer wavelength region are inorganic compounds such as Se/Te, Se/As and CdSe. Many of these inorganic compounds are designated as poisons, dangerous drugs or special chemical substances under regulations that require utmost care in handling, particularly in disposal. Furthermore, these compounds are difficult to manufacture and their production cost is high. As another disadvantage, they have no flexibility and can only be shaped into a belt form with great difficulty.

Energetic efforts have been made in the study of electrophotographic photoreceptors using organic disperse photosensitive materials wherein a charge generation layer and a charge transport layer are laminated on an electrically conductive support. For example, U.S. Pat. No. 4,018,953 discloses an electrophotographic photoreceptor having a charge generation layer containing an organic photoconductive materials such as phthalocyanine type pigments, quinacridones, etc. and a charge transport layer having a specific aromatic diamine dispersed in a binder (hereafter referred to as "double-layered photoreceptor"). Double-layered photoreceptors using other organic disperse photosensitive materials are also described in U.S. Pat. Nos. 4,050,935, 4,127,412, 4,173,472, 4,175,960 and 4,284,699. Several authors have reported that phthalocyanine in the form of a disperse photosensitive material exhibits excellent electrophotographic characteristics (U.S. Pat. Nos. 4,018,953 and 4,181,772). Organic phthalocyanine compounds are non-toxic and inexpensive, but they have low sensitivity to light below 550 nm and are difficult to purify. No practical phthalocyanine compound has been found that exhibits flat photosensitivity characteristics over the visible to near infrared region.

U.S. Pat. No. 3,824,099 discloses a double-layered photoreceptor having a charge generation layer containing squaric acid pigments dispersed in a binder and a charge transport layer of tri-aryl pyrazoline, and U.S. Pat. No. 4,123,270 discloses a photoreceptor having a charge generation layer containing derivatives of squaric acid pigments which are soluble in an organic primary amine. The squaric acid pigments used in these U.S. Patents are represented by the formula

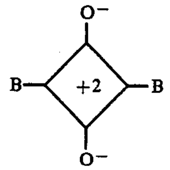

wherein B is

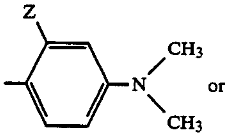

or

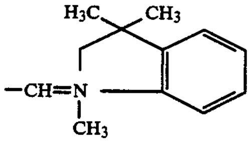

, and Z is a hydrogen atom, a hydroxy group or a methyl group. However, these squaric acid pigments still have defects in that charge retention is low and residual potential is high, resulting in low image density and high fog density. Further, the squaric acid pigments do not exhibit flat photosensitivity characteristics over the visible to near infrared region.

SUMMARY OF THE INVENTION

One object of the present invention is to provide an extremely highly sensitive photoconductive material that can be used with any of the existing electrophotographic processes and which has spectral sensitivity over the visible to infrared region, high charge retention and low residual potential.

A second object of the invention is to provide a process for the production of this photoconductive material.

Another object of the present invention is to provide a highly sensitive and mechanically strong (e.g., high wear resistance) photoreceptor for electrophotography that is free from the defects (i.e., low wear resistance and insufficient mechanical strength) of a poly(vinylcarbazole)trinitrofluorenone type light-sensitive material and which has substantially flat spectral sensitivity characteristics extending from the visible to near infrared region.

The present inventors have made various studies to obtain a photoconductive material that is free from the defects of the conventional inorganic photosensitive materials, organic photosensitive materials and organic disperse photosensitive materials and which instead have excellent electrophotographic characteristics and flexibility, and which exhibit high sensitivity over a wide range covering the visible and near infrared wavelengths. As a result, the inventors have found that the above objects are attained by novel squarylium compounds represented by the following formulae (I) or (II):

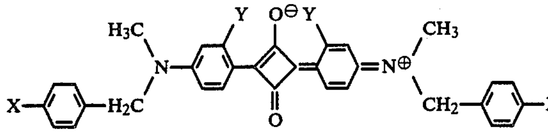
(I)

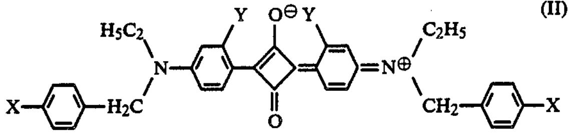
(II)

wherein X is a hydrogen atom, an alkyl group having 1 to 6 carbon atoms (preferably a straight-chain alkyl group), a hydroxy group, an alkoxy group having 1 to 4 carbon atoms, or a halogen atom; Y is a hydrogen atom, an alkyl group having 1 to 4 carbon atoms, a hydroxy group or an alkoxyl group having 1 to 4 carbon atoms.

The squarylium pigment of formula (I) or (II) is obtained by reacting 3,4-dihydroxy-3-cyclobutene-1,2-dione of formula (III) (hereinafter referred to as "squaric acid"):

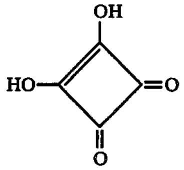
(III)

with an aniline derivative of formula (IV):

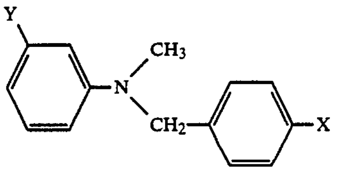
(IV)

wherein X and Y are as defined in general formula (I).

The corresponding squarylium pigment of formula (II) is obtained by reacting squaric acid with an aniline derivative of the formula (V):

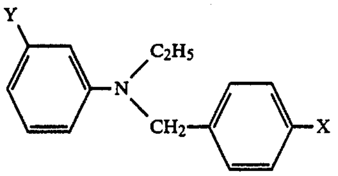
(V)

wherein X and Y are as defined in general formula (II).

DETAILED DESCRIPTION OF THE INVENTION

Figure 1:
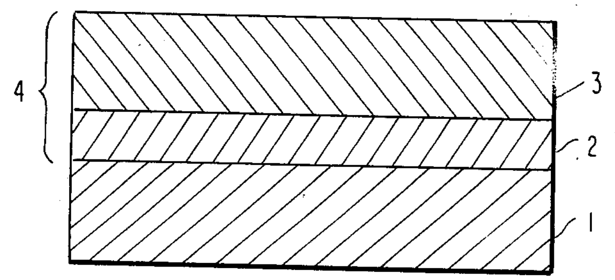
FIGS. 1 and 2 are cross sections of illustrative layer arrangements of the electrophotographic photoreceptor of the present invention.

In general formula (II), the halogen atom for X is preferably a fluorine atom, a chlorine atom or a bromine atom.

In the process according to the invention, the compounds represented by general formulae (I) and (II) are obtained by reacting squaric acid with the aniline derivative in a solvent (e.g., n-butanol or amyl alcohol) for about 3-5 hours at an oil bath temperature of not more than 150° C., preferably 120°-140° C. The solvent may be used as admixture with a low boiling point solvent (e.g., benzene, toluene, etc.). If the reaction temperature is more than 150° C., the reaction products may be decomposed. The resulting compound is washed and purified by recrystallization from a suitable solvent.

Specific examples of the so prepared novel squarylium compound of formula (I) of the present invention are identified below by their structural formulae, although the present invention is not to be construed as being limited thereto.

| Structural formula | Compound No. |
|---|---|
| 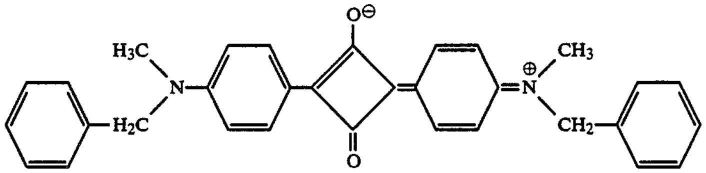 | (1) |
| 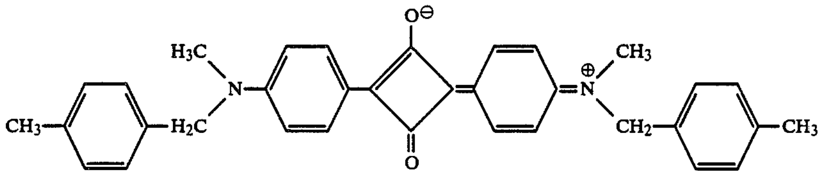 | (2) |

-continued

| Structural formula | Compound No. |
|---|---|
| 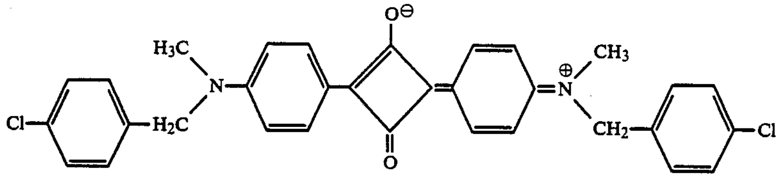 | (3) |
| 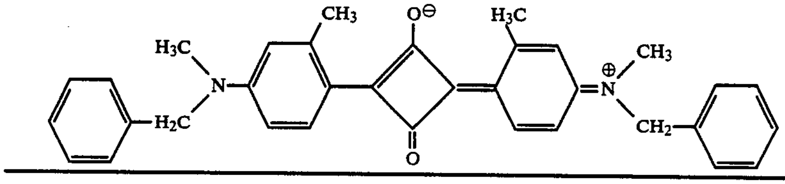 | (4) |

Processes for producing the novel squarylium compounds of the present invention are described by the following synthesis examples, although the present invention is not to be construed as being limited thereto.

Synthesis Example 1 (Preparation of Compound (1))

N-Benzyl-N-methylaniline (2.48 g) and 3,4-dihydroxy-3-cyclobutene-1,2-dione (0.76 g) were added to n-butanol (26.8 ml). The resulting mixture was heated at 130°-140° C. for 4 hours under agitation. After cooling, the resulting brilliant pale green crystal was collected by filtration, washed with methanol, and dried to obtain 0.85 g of the desired squarylium compound (1) (26.8%). Analysis of compound (1) revealed the following characteristics:

Decomposition point: 259° C.

IR absorption spectrum (KBr tablet):

$\nu_{c=o}=1590\ cm^{-1}$

Elemental analysis:

| | Found | Calculated |
|---|---|---|
| C | 81.27% | 81.33% |
| H | 5.86% | 5.97% |
| N | 6.02% | 5.93% |

Visible light absorption spectrum:

$\lambda max=633$ nm (in dichloromethane).

Synthesis Examples 2 to 4 (Preparation of Compounds (2)-(4))

In the same manner as in Synthesis Example 1, the reaction between 3,4-dihydroxy-3-cyclobutene-1,2-dione and the aniline derivative was performed, using the different aniline derivatives shown in Table 1. Table 1 shows data on the compounds produced in Synthesis Examples 2 to 4 with respect to the decomposition point, IR absorption spectrum and visible light absorption spectrum. Table 2 shows the results of elemental analysis of these compounds.

TABLE 1

| Compound No. | Aniline derivative | Decomposition point | IR absorption spectrum | Visible light absorption spectrum* |
|---|---|---|---|---|
| (2) | 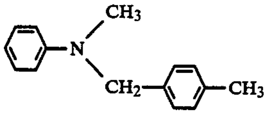 | 261° C. | 1585 $cm^{-1}$ | 634 nm |
| (3) | 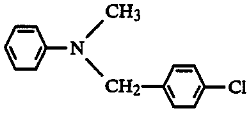 | 266° C. | 1590 $cm^{-1}$ | 631 nm |
| (4) | 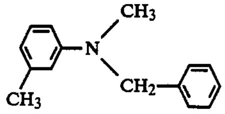 | 257° C. | 1580 $cm^{-1}$ | 649 nm |

Note
*in dichloromethane

TABLE 2

| Compound No. | Molecular formula | | Found | Calculated |
|---|---|---|---|---|
| (2) | $C_{34}H_{32}N_2O_2$ | C | 81.45% | 81.57% |
| | | H | 6.46% | 6.44% |
| | | N | 5.62% | 5.60% |
| (3) | $C_{32}H_{26}N_2O_2Cl_2$ | C | 71.14% | 70.97% |
| | | H | 4.80% | 4.84% |
| | | N | 5.01% | 5.18% |
| | | Cl | 13.03% | 13.13% |
| (4) | $C_{34}H_{32}N_2O_2$ | C | 81.42% | 81.57% |
| | | H | 6.33% | 6.44% |

TABLE 2-continued

| Compound No. | Molecular formula | | Found | Calculated |
|---|---|---|---|---|
| | | N | 5.57% | 5.60% |

The novel squarylium compounds thus prepared are effective for use as charge generation materials in a multi-layered photoreceptor.

These compounds exhibit flat characetristics in the spectral sensitivity over the range of 400–850 nm, and they have sufficient sensitivity to light in both the visible and near infrared regions.

Therefore, the novel squarylium compounds of the present invention may be used not only with conventional electrophotographic copiers but also with semiconductor laser printers in intelligent copiers. The use of these compounds is not limited to electrophotography; they may also be used with optical recording mediums (e.g., laser discs) and organic solar cells.

The squarylium pigments of formulae (I) and (II) can be used in multi-layered photoreceptors in electrophotography. More specifically, the squarylium pigment is incorporated in the charge generation layer of a double-layered photoreceptor, and combined with a known charge transport layer which typically is composed of a photoconductive polymer such as poly(vinyldibenzothiophene), poly(vinylpyrene), poly(vinylanthracene) or poly(vinylcarbazole), or which has triarylpyrazoline, triphenylmethane, oxadiazole, tetraphenylbenzidine or trinitrofluorenone incorporated in a binder resin, as described in U.S. Pat. Nos. 4,018,953 and 4,150,987. The binder resin for the charge transport layer may be selected from those described later as a binder for the charge generation layer, and those described in U.S. Pat. Nos. 3,121,006, 3,870,516, 4,018,953, 4,284,699 and 4,173,472 may also be used. The so prepared photoreceptor has improved charge retention, reduced residual potential and enhanced mechanical strength.

Figure 2:
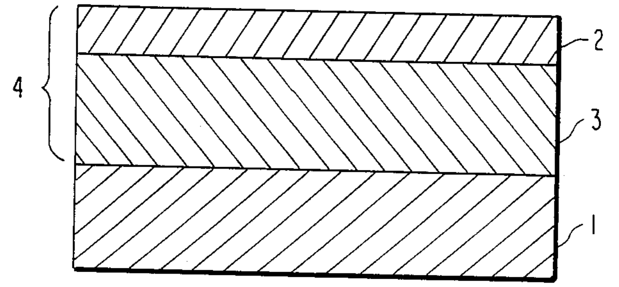

Two typical embodiments of the double-layered photoreceptor for use in electrophotographic process are illustrated in FIGS. 1 and 2, wherein an electrically conductive support 1 is coated with a light-sensitive layer 4 composed of an assembly of a charge generation layer 2 containing the squarylium pigment and a charge transport layer 3 containing a charge transport material. The thickness ratio of the charge generation layer to the charge transport layer is preferably from about ½ to about 1/200. Further, the squarylium pigment and a charge transport material may be incorporated into one layer to form a single-layered photoreceptor, if desired.

The squarylium pigment in the charge generation layer may be used either alone or in combination with a suitable binder resin. In the latter case, the pigment is generally used in an amount of about 10–90 wt%, preferably about 10–50 wt%, of the weight of charge generation layer, and the pigment is dispersed in the form of particles in the binder resin.

If the squarylium pigment alone is used, the charge generation layer may be prepared by solvent coating or vacuum vapor deposition.

The thickness of the charge generation layer generally ranges from about 0.1 to 3μ, preferably about 0.2 to 1μ.

For the purpose of its dispersion in a binder, the pigment may be ground into fine particles by a known method using any conventional mill, such as an SPX MILL, ball mill or RED DEVIL (trade name). Particle size of the pigment is generally not more than 5μ, preferably 0.01 to 3μ, but the particle size is not limited thereto.

The binder used in the charge generation layer may or may not be photoconductive by itself. Illustrative photoconductive binders are photoconductive polymers such as poly(vinylcarbazole), poly(vinylcarbazole) derivatives, poly(vinylnaphthalene), poly(vinylanthracene) and poly(vinylpyrene), as well as organic matrix materials having the charge transporting capability.

Known insulating resins having no photoconductivity may also be used as a binder. Illustrative known insulating resins include polystyrene, polyesters, poly(vinyltoluene), poly(vinylanisole), poly(chlorostyrene), poly(vinylbutyral), poly(vinyl acetate), poly(vinylbutyl methacrylate), copoly(styrene-butadiene), polysulfone, copoly(styrene-methyl methacrylate), and polycarbonates.

In order to further improve the mechanical strength of the photoreceptor, plasticizers may be used as in the case of general polymeric materials. Suitable plasticizers include chlorinated paraffin, chlorinated biphenyl, and phosphate and phthalate compounds. These plasticizers may be used in an amount of about 0–10 wt% of the binder, achieving the intended object of providing further improved mechanical strength without compromising the sensitivity or electrical properties of the receptor.

The binder having the squarylium pigment dispersed therein is coated onto the electrically conductive support. Any known coating technique such as immersion coating, spray coating, bar coating and applicator coating may be employed for the purpose of providing the desired charge generation layer.

Usable electrically conductive supports include metals (e.g., aluminum, nickel, chromium, iron, stainless, copper, etc.), paper which is rendered electrically conductive, as well as polymeric films and glass plates having an electrically conductive coat of the above metals, Au, Ag, indium oxide, indium tin oxide, etc.

A surface layer such as a protective layer and an insulating layer may further be provided on the light-sensitive layer so as to prevent mechanical damage and chemical change in properties of the light-sensitive layer. The protective layer is a layer having low electric resistance of $10^8$ to $10^{14}$ Ωcm which can be used in so-called Carlson process, and the insulating layer is an electrically insulating layer which can be used in a process as described in U.S. Pat. Nos. 3,401,167 and 3,438,706. Both layers are substantially transparent to light for exposure and the thicknesses of the protective layer and the insulating layer are about 2 to 20μ and about 10 to 40μ, respectively.

In order to prevent injection of electron from an electrically conductive support to the light-sensitive layer, a barrier layer may be formed between the support and the light-sensitive layer. For the purpose, aluminum oxide, nylon, epoxy resins can be used. Such a barrier layer may not be formed when the photoreceptor is used in the process of U.S. Pat. Nos. 3,041,167 and 3,438,706 as described above or when the charge transport layer is formed as a lower layer on the support in the preparation of double-layered photoreceptor (FIG. 2). An adhesive layer may also be formed between the support and the light-sensitive layer to improve adhesion therebetween.

The electrophotographic photoreceptor of the present invention may be used not only with ordinary copiers but also with laser printers, as well as intelligent copiers since the photoreceptor of the present invention is sensitive to laser. Laser which can be applied to the photoreceptor of the present invention is preferably a semiconductor laser such as those of Ga-As type semiconductors (e.g., Ga-As, Al-Ga-As, Ga-As-P, etc.).

Specific embodiments of the present invention are further described by reference to working examples, which are not to be construed as limiting the scope of the invention. Unless otherwise indicated, all parts, percents and ratios are by weight, and surface potential Vo given is an absolute value.

EXAMPLE 1

10 g of squarylium pigment (3) of formula (I) wherein X=Cl and Y=H was ground in a ball mill for 12 hours in the presence of 160 ml of methylene chloride. The ground particles (30 wt%) having an average particle size of 0.1 μm were added to a polyester resin (tradename "Vylon 200"; weight average molecular weight 15,000) and mixed therewith. The resulting mixture was coated onto an aluminum plate by an applicator to form a charge generation layer in a dry thickness of about 0.5 μm. A mixture of 50 wt% of 1-phenyl-3-(p-diethylaminostyryl)-5-(p-diethylaminophenyl)pyrazoline with a polycarbonate resin (tradename "Panlite"; weight average molecular weight 28,000) was coated onto the charge generation layer by an applicator, so as to form a charge transport layer in a thickness of about 15 μm.

The photoreceptor was mounted in a paper analyzer (product of Kawaguchi Electric Works Co., Ltd.) and charged to a negative voltage of 6 kV by corona discharge that continued for 2 seconds. The photoreceptor was then left in the dark for 2 seconds and the resulting surface potential Vo was measured. Subsequently, the photoreceptor was exposed to a tungsten halide lamp (10 lx) until the surface potential dropped to ½ Vo. By this procedure, the half exposure (E½) in seconds of the photoreceptor was determined. The results were as follows:

$$Vo=800\ V,\ E\tfrac{1}{2}=1.9\ lx.sec.$$

In order to examine the sensitivity of the photoreceptor to infrared light, the photoreceptor was exposed to light having a wavelength of 800 nm after charging, and the half exposure (E½) was measured. As a result, it was 8.2 erg/cm².

For comparision, a photoreceptor was prepared in the same manner except that squarylium pigment (3) was replaced by squarylium pigment (C-1) shown below, which corresponds to those of U.S. Pat. No. 3,824,099.

(C-1)

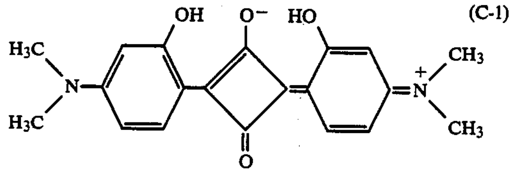

The half exposures with respect to tungsten halide light and light having a wavelength of 800 nm of the comparative photoreceptor were 1.7 lx.sec. and 9.7 erg/cm², respectively.

It is clearly seen from the results that the photoreceptor using the squarylium pigment of the present invention is superior to the photoreceptor using a conventional squarylium pigment in photosensitivity, particularly to light of infrared region.

EXAMPLES 2 AND 3

Photoreceptors were prepared as in Example 1 except that squarylium pigment (3) was replaced by squarylium pigment (5) of formula (I) wherein X=Cl and Y=$CH_3$, and squarylium pigment (6) wherein X=Cl and Y=OH. The electrical properties of the two samples are shown in Table 3.

TABLE 3

| Ex. No. | Pigment | Vo (V) | E½ (lx. · sec.) |
|---|---|---|---|
| 2 | (5)* | 780 | 2.4 |
| 3 | (6)* | 720 | 2.8 |

Note
*(5)

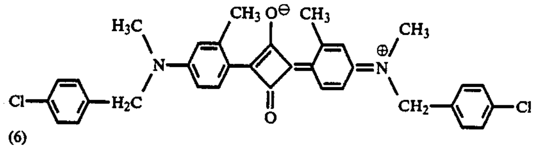

(6)

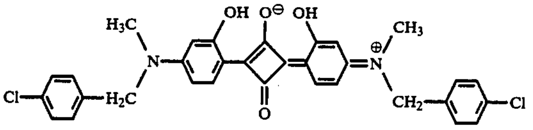

EXAMPLES 4 TO 6

Photoreceptors were prepared as in Example 1 except that squarylium pigment (3) was replaced by squarylium pigments (1), (4) and (7) of formula (I) wherein X=H, and Y=H, $CH_3$ and OH, respectively. The electrical properties of the three samples are shown in Table 4.

TABLE 4

| Ex. No. | Pigment | Vo (V) | E½ (lx · sec.) |
|---|---|---|---|
| 4 | (1) | 820 | 2.1 |
| 5 | (4) | 790 | 2.5 |
| 6 | (7)* | 750 | 2.6 |

Note
*(7)

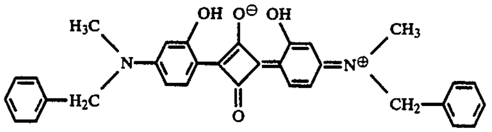

EXAMPLES 7 TO 12

As in Examples 1 to 6 and using the squarylium pigments listed in Table 5, photoreceptors were prepared except that the charge generation layer was formed on, rather than under, the charge transport layer. The electrical properties of the samples are shown in Table 5.

TABLE 5

| Ex. No. | Pigment | Vo (V) | E½ (lx. sec.) |
|---|---|---|---|
| 7 | (3) | 770 | 2.0 |
| 8 | (5) | 760 | 2.6 |
| 9 | (6) | 690 | 3.5 |
| 10 | (1) | 790 | 2.4 |

TABLE 5-continued

| Ex. No. | Pigment | Vo (V) | E½ (lx. sec.) |
|---|---|---|---|
| 11 | (4) | 780 | 2.7 |
| 12 | (7) | 710 | 3.0 |

EXAMPLE 13

A photoreceptor was prepared in the same manner as in Example 1, with the exception that squarylium pigment (8) of formula (II), wherein X=Cl, and Y=H, was used in the charge generation layer instead of pigment (3) of formula (I).

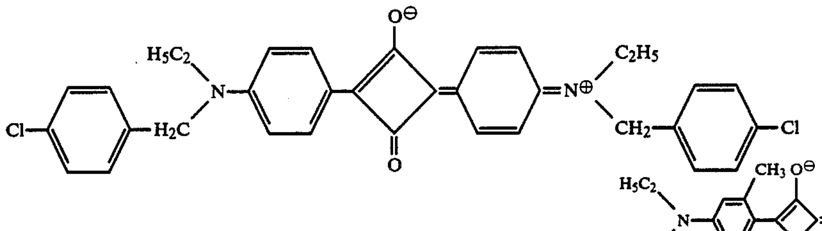

(8)

When evaluated in the same manner as in Example 1, the results were as follows:

Vo=640 V, $E\frac{1}{2}$=3.4 lx.sec.

EXAMPLES 14 AND 15

Photoreceptors were prepared as in Example 13 except that squarlium pigment (8) was replaced by squarylium pigment (9) of formula (II) wherein X=Cl and Y=$CH_3$, and squarylium pigment (10) of formula (II) wherein X=Cl and Y=OH. The electrical properties of the two samples are shown in Table 6

TABLE 6

| Ex. No. | Pigment | Vo (V) | E½ (lx · sec.) |
|---|---|---|---|
| 14 | (9)* | 620 | 4.1 |
| 15 | (10)* | 690 | 3.2 |

Note

*(9)

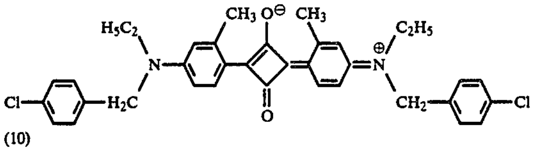

(10)

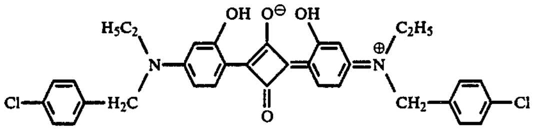

EXAMPLES 16 TO 18

Photoreceptors were prepared as in Example 13 except that squarylium pigment (8) was replaced by squarylium pigments (11), (12) and (13) of formula (II) wherein X=H, and Y=H, $CH_3$ and OH, respectively. The electrical properties of these samples are shown in Table 7.

TABLE 7

| Ex. No. | Pigment | Vo (V) | E½ (lx · sec.) |
|---|---|---|---|
| 16 | (11)* | 630 | 3.9 |
| 17 | (12)* | 620 | 5.0 |
| 18 | (13)* | 650 | 3.5 |

Note

*(11)

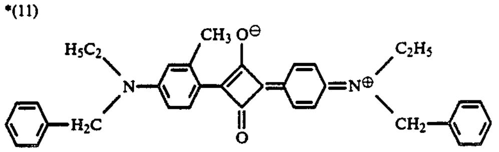

(12)

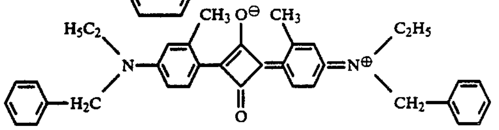

(13)

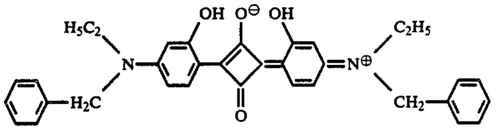

EXAMPLES 19 TO 24

As in Examples 13 to 18 and using squarylium pigments (8) to (13), photoreceptors were prepared except that the charge generation layer was formed on, rather than under, the charge transport layer. The electrical properties of the samples are shown in Table 8.

TABLE 8

| Ex. No. | Pigment | Vo (V) | E½ (lx. sec.) |
|---|---|---|---|
| 19 | (8) | 620 | 4.0 |
| 20 | (9) | 610 | 5.5 |
| 21 | (10) | 650 | 4.0 |
| 22 | (11) | 620 | 4.4 |
| 23 | (12) | 590 | 6.0 |
| 24 | (13) | 630 | 4.3 |

EXAMPLES 25-30 AND COMPARATIVE EXAMPLES 1-3

10 g of squarylium pigment shown in Table 9 was ground in a ball mill for 12 hours in the presence of 160 ml of methylene chloride. The ground particles (30 wt%) having an average particle size of 0.1 μm were added to a polyester resin (tradename "Vylon 200") and mixed therewith. The resulting mixture was coated onto an aluminum tube by an applicator to form a charge generation layer in a dry thickness of about 2 μm. Then, a mixture of 50 wt% of 1-phenyl-3-(p-diethylaminostyryl)-5-(p-diethylaminophenyl)-pyrazoline with a polycarbonate resin (tradename "Panlite") was coated onto the charge generation layer by an applicator, so as to form a charge transport layer in a dry thickness of about 20 μm.

The photoreceptor was charged to a negative voltage using corotron of 40 μA and charge retention of the photoreceptor was measured. Then, the photoreceptor was subjected to uniform exposure to light and residual potential was measured. Further the procedures of negative charging and light-exposure was repeated 10 times and the resulting residual potential of the photoreceptor was measured. The results are shown in Table 9.

TABLE 9

| Ex. No. | Pigment | Charge Retention (V) | Residual potential Initial stage | Residual potential After 10-time processings |
|---|---|---|---|---|
| 25 | (3) | 720 | 10 | 30 |
| 26 | (5) | 710 | 20 | 40 |
| 27 | (6) | 695 | 35 | 70 |
| 28 | (7) | 705 | 20 | 55 |
| 29 | (8) | 615 | 50 | 95 |
| 30 | (12) | 600 | 50 | 105 |
| Comp. Ex. 1 | (C-2)* | 300 | 100 | 180 |
| Comp. Ex. 2 | (C-1) | 410 | 110 | 190 |
| Comp. Ex. 3 | (C-3)* | 800 | 200 | 750 |

Note
*(C-2)

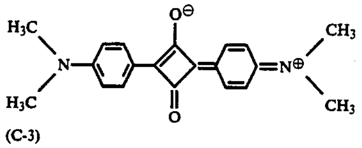

(C-3)

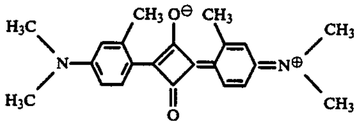

It is seen from the results that the photoreceptors using the squarylium pigments of the present invention exhibit excellent electrophotographic properties that the charge retention is as high as −600 to −720 V and the residual potential is low at the initial stage (−10 to −50 V) and even after the 10-time processings (−30 to −105 V). On the other hand, the photoreceptors of Comparative Examples 1 and 2 exhibit low charge retention and high residual potential so that they can only provide an image having low image density with high fog density and having poor image reproducibility. Although the photoreceptor of Comparative Example 3 exhibit high charge retention, the photoreceptor cannot provide an image after repeated use because of high residual potential after 10-time processings which is more or less the same as its charge retention (i.e., more or less the same in density at image areas and non-image areas).

The photoreceptors using the squarylium pigments of the present invention exhibit flat photosensitivity characteristics over the visible to infrared region, in other words, exhibit improved sensitivity to light of infrared region. Further since the photoreceptors of the present invention possess high charge retention and low residual potention even after repeated use, high contrast electric latent image can be formed upon electrophotographic processings, resulting in the formation of image having high image density with minimized fog density and having good image reproducibility. Futhermore the squarylium pigments of the present invention is excellent with respect to non-toxicity.

While the invention has been described in detail and with reference to specific embodiments thereof, it will be apparent to one skilled in the art that various changes and modifications can be made therein without departing from the spirit and scope thereof.

What is claimed is:

1. A novel squarylium compound of general formulae (I) or (II):

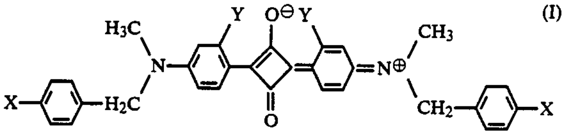

(I)

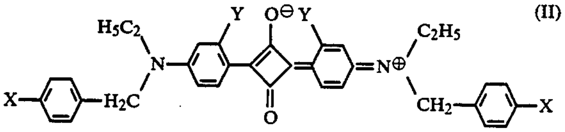

(II)

wherein X is a hydrogen atom, an alkyl group having 1 to 6 carbon atoms, a hydroxyl group, an alkoxy group having 1 to 4 carbon atoms, or a halogen atom; Y is a hydrogen atom, an alkyl group having 1 to 4 carbon atoms, a hydroxyl group, or an alkoxy group having 1 to 4 carbon atoms.

2. Process for producing a squarylium compound of the following general formula (I):

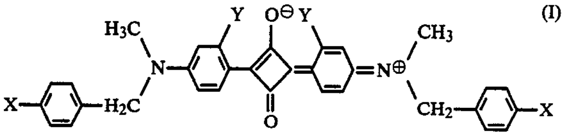

(I)

comprising reacting 3,4-dihydroxy-3-cyclobutene-1,2-dione of formula (III):

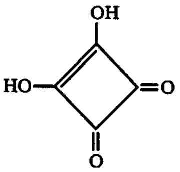

(III)

with an aniline derivative of formula (IV):

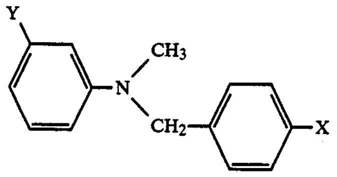

(IV)

wherein X is a hydrogen atom, an alkyl group having 1 to 6 carbon atoms, a hydroxyl group, an alkoxy group having 1 to 4 carbon atoms, or a halogen atom; Y is a hydrogen atom, an alkyl group having 1 to 4 carbon atoms, a hydroxyl group or an alkoxy group having 1 to 4 carbon atoms.

3. Process for producing a squarylium compound of the following general formula (II):

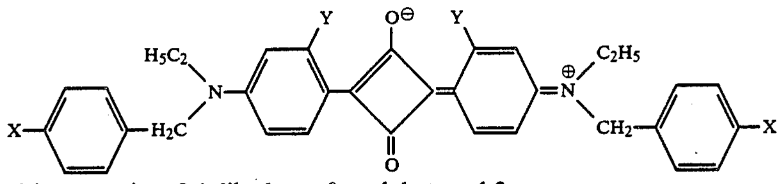

(II)

comprising reacting 3,4-dihydroxy-3-cyclobutene-1,2-dione of the formula (III):

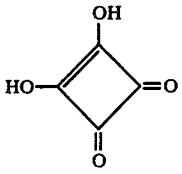

(III)

with an aniline derivative of the formula (V):

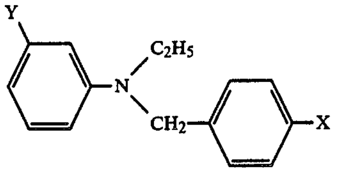

(V)

wherein X is a hydrogen atom, an alkyl group having 1 to 6 carbon atoms, a hydroxyl group, an alkoxy group having 1 to 4 carbon atoms, or a halogen atom; Y is a hydrogen atom, an alkyl group having 1 to 4 carbon atoms, a hydroxyl group or an alkoxy group having 1 to 4 carbon atoms.

4. The process claimed in claim 2, wherein said reaction is conducted in a solvent selected from the group consisting of n-butanol and amyl alcohol at a temperature of not more than 150° C., and said compound is washed and purified by recrystallization from a solvent.

5. The process claimed in claim 3, wherein said reaction is conducted in a solvent selected from the group consisting of n-butanol and amyl alcohol at a temperature of not more than 150° C., and said compound is washed and purified by recrystallization from a solvent.

6. The process claimed in claim 4, wherein said reaction is conducted at atmospheric pressure.

7. The process claimed in claim 5, wherein said reaction is conducted at atmospheric pressure.

8. The squarylium compound of claim 1, wherein X is a hydrogen atom or a halogen atom.

9. The process of claim 2, wherein X is a hydrogen atom or a halogen atom.

10. The process of claim 3, wherein X is a hydrogen atom or a halogen atom.

* * * * *